United States Patent
John et al.

(10) Patent No.: US 6,518,424 B1
(45) Date of Patent: Feb. 11, 2003

(54) SUBSTITUTED PYRIMIDINE COMPOSITIONS AND METHODS OF USE

(75) Inventors: Varghese John, San Francisco, CA (US); Russell E. Rydel, Belmont, CA (US); Michael S. Dappen, Redwood City, CA (US); Eugene D. Thorsett, Moss Beach, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/438,103

(22) Filed: Nov. 10, 1999

Related U.S. Application Data
(60) Provisional application No. 60/108,192, filed on Nov. 12, 1998.

(51) Int. Cl.[7] ................... C07D 239/24; C07D 239/34; C07D 239/47; A61K 21/505
(52) U.S. Cl. ................ 544/242; 544/319; 544/326; 514/256; 514/269
(58) Field of Search .................... 544/242, 319, 544/320, 326; 514/256, 269

(56) References Cited

FOREIGN PATENT DOCUMENTS

| CA | 2027839 | 4/1991 |
| EP | 424 317 | 4/1991 |
| EP | 468 054 | 1/1992 |

OTHER PUBLICATIONS

Ackermann, Elizabeth J. et al., "Inhibition of Macrophage Ca$^2$+–independent Phospholipase A2 by Bromoenol Lactone and Trifluoromethyl Ketones," *The Journal of Biological Chemistry* 270(1):445–450 (Jan. 1995).

Oinuma, Hitoshi et al. "Synthesis and Biological Evaluation of Substituted Benzenesulfonamides as Novel Potent Membrane–Bound Phospholipase A2 Inhibitors," *J. Med. Chem.* 34:2260–2264 (1991).

Street, Ian P. et al. "Slow–and Tight–Binding Inhibitors of the 85–kDa Human Phospholipase A2," *Biochemistry* 32:5935–5940 (1993).

Aroyan, A. et al., "Pyrimidine derivatives. Substituted 6-(4'-Alkoxybenzyl) Pyrimidines," *Chemical Abstracts*, vol. 75, No. 7, Abstract No. 49022w, 1971.

*Primary Examiner*—Richard L. Raymond
*Assistant Examiner*—Venkataraman Balasubramanian
(74) *Attorney, Agent, or Firm*—Townsend and Townsend and Crew LLP (57) ABSTRACT

Substituted pyrimidines that have the general structure:

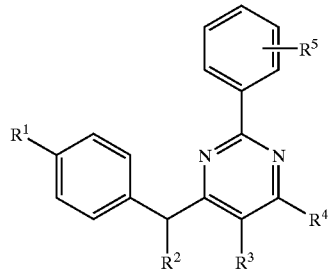

(I)

in which the symbol $R^1$ represents a $C_1$–$C_6$ alkyl, $C_1$–$C_6$ alkoxy or halogen atom; $R^2$ represents a phenyl group, substituted phenyl group, benzyl moiety, substituted benzyl moiety, $C_3$–$C_7$ cycloalkyl, or substituted $C_3$–$C_7$ cycloalkyl; $R^3$ represents a hydrogen or $C_1$–$C_6$ alkyl group, $R^4$ represents —H, —OH, —$N_3$ or —NHCOCH$_3$; and $R^5$ represents H are provided. These compounds have activity as inhibitors of phospholipase $A_2$, and are useful in treating disorders mediated by phospholipase $A_2$.

18 Claims, 7 Drawing Sheets

SUBSTITUTED PYRIMIDINE COMPOSITIONS AND METHODS OF USE

CROSS-REFERENCES TO RELATED APPLICATIONS

This application claims priority to U.S. Provisional Patent Application No. 60/108,192, filed Nov. 12, 1998, the disclosure of which is incorporated by reference in its entirety for all purposes.

FIELD OF THE INVENTION

The present invention provides novel substituted pyrimidines. These compounds have been found to inhibit phospholipase $A_2$ activity, in particular $cPLA_2$ (cytosolic phospholipase $A_2$).

BACKGROUND OF THE INVENTION

Phospholipases $A_2$ ($PLA_2$s; EC 3.1.1.4) are enzymes that hydrolyze the 2-acyl ester bond of phosphoglycerides generating free fatty acids and lysophospholipids (for review, see, Kramer, R M (1993) *Advances in Second Messenger and Phosphoprotein Research* 28: 81; Glaser et al. (1993) *TiPS* 14: 92; Dennis E A (1994) *J. Biol. Chem.* 269: 13057). $PLA_2$s are a diverse class of enzymes with regard to function, localization, regulation, mechanism, sequence, structure, and role of divalent metal ions. A variety of polypeptide species can exhibit $PLA_2$ activity; for purposes of this specification, these polypeptides are considered $PLA_2$ isozymes.

In general, $PLA_2$ enzymes catalyze the hydrolysis of the fatty acid ester bond at the sn-2 position of membrane phospholipids to produce arachidonic acid and its metabolites. Group I, II, and III $PLA_2$s are extracellular enzymes of approximately 14–18 kD in humans, and are designated $sPLA_2$s, in recognition of their secretion. $sPLA_2$s are found in many extracellular fluids and have a broad substrate specificity for many types of phospholipids.

Group IV $PLA_2$ is a cytosolic enzyme of approximately 85 kD (based on deduced cDNA coding sequence) to 110 kD (based on SDS-PAGE of purified protein), and is designated $cPLA_2$ to indicate its cytosolic location. Unlike $sPLA_2$s, the $cPLA_2$ enzyme exhibits preferential catalysis of phospholipids which contain arachidonic acid, and is most likely the enzyme responsible for arachidonic acid release which is the rate-limiting step for subsequent eicosanoid biosynthesis of pro-inflammatory lipid mediators (prostaglandins, leukotrienes, lipoxins, and platelet-activating factor: "PAF"). $cPLA_2$ is present in the cytosol of a variety of species and cell types, including human U937 cells (monocytes), platelets, kidney, and macrophages, among others, and is implicated in controlling arachidonic acid metabolism and eicosanoid production.

Some cells contain calcium independent phospholipase $A_2$/B enzyme. The phospholipase $A_2$/B purified enzyme is characterized by activity in the absence of calcium and having a molecular weight of 86 kD on SDS-PAGE (see, U.S. Pat. Nos. 5,554,511 and 5,466,595).

Of particular interest in the present invention is the $cPLA_2$ enzyme. Human $cPLA_2$ has been cloned as a cDNA isolated from mRNA of a human monocytic cell line, (U.S. Pat. Nos. 5,354,677 and 5,328,842; Sharp et al. (1991) *J. Biol. Chem.* 266: 14850; Clark et al. (1991) *Cell* 65: 1043) and the mRNA encodes a protein of 749 amino acids which has little detectable homology with the secreted $sPLA_2$s or any other protein in known sequence databases. The $cPLA_2$ cDNA identifies a single copy gene in the human genome, with no detectable closely related genes based on Southern blotting experiments. A suitable source of $cPLA_2$ can be obtained, if desired, by expression of a recombinant expression vector in a suitable host cell, as described in U.S. Pat. No. 5,354,677, or by conventional biochemical purification from mammalian cells, as is known in the art.

Moreover, $cPLA_2$ contains an amino-terminal domain which binds calcium and similar divalent cations, and $cPLA_2$ binds to membrane vesicles at submicromolar concentrations of $Ca^{+2}$ in a calcium-dependent fashion. $cPLA_2$ can translocate to membranes when activated in the presence of calcium. Presumably, $cPLA_2$ associates with membrane components in vivo under suitable calcium concentrations. Agents that stimulate the release of arachidonic acid (ATP, thrombin, phorbol ester, calcium ionophore) can cause increased serine phosphorylation of $cPLA_2$ which increases the enzymatic activity of $cPLA_2$ (Lin et al. (1993) *Cell* 72: 269). Phosphorylation is believed to contribute to the control of $cPLA_2$ activity in vivo (Lin et al. (1992) *Proc. Natl. Acad. Sci. (USA)* 89: 6147; Lin et al. (1993) *Cell* 72: 269; Qiu et al. (1993) *J. Biol. Chem.* 268: 24506; Kramer et al. (1993) *J Biol. Chem.* 268: 26796).

The art generally recognizes the physiologic role of $cPLA_2$ to be in the mediation of inflammation via its role in arachidonic acid metabolism and lipid/lipoprotein metabolism, such as cell membrane homeostasis. Roshak et al. (1994) *J. Biol. Chem.* 269: 25999 used antisense oligonucleotides complementary to the $cPLA_2$ mRNA to inhibit prostaglandin production in LPS-induced monocytes, indicating a potential role for $cPLA_2$ in generating inflammatory regulators in monocytes. Verity MA (1993) *Ann. N.Y. Acad. Sci.* 679:110 speculates that "abusive activation" of $PLA_2$ via uncontrolled $Ca^{+2}$ influx might produce irreversible cell injury of neurons via extensive localized lipid peroxidation and subsequent membrane disintegration. U.S. Pat. Nos. 5,354,677 and 5,328,842 indicates that $cPLA_2$ inhibitors are expected to be used to treat inflammatory conditions, such as psoriasis, asthma, and arthritis (see, col. 15), and prophesies that such anti-inflammatory compounds can be identified as $cPLA_2$ inhibitors.

In addition to the roles mentioned above, $PLA_2$ activity has been implicated as a contributor to destructive cellular processes in various tissues including, but not limited to, the central nervous system. $PLA_2$ activity has also been reportedly involved in ischemic injury and pathological nervous system conditions.

A number of inhibitors of $PLA_2$ activity have been reported. Bromoenol lactone and trifluoromethyl ketones (e.g., palmitoyl trifluoromethyl ketone, arachidonyl trifluoromethyl ketone) have been reported to be capable of inhibiting a $Ca^{+2}$-independent $PLA_2$ activity (Ackermann et al. (1995) *J. Biol. Chem.* 270: 445) as well as $cPLA_2$ (Street et al. (1993) *Biochemistry* 32: 5935). Several benzenesulfonamide derivatives have also been reported to be capable of inhibiting $PLA_2$ activity (European Patent Application 468 054; Oinuma et al. (1991) *J. Med. Chem.* 34: 2260).

In view of the role $PLA_2$ can play in destructive cellular processes, there is a need in the art for new compounds that are inhibitors of $PLA_2$. These compounds can then be used to treat or prevent $PLA_2$-mediated diseases. The present invention provides such new compounds, compositions and methods of treatment.

SUMMARY OF THE INVENTION

The present invention provides substituted pyrimidines which are effective inhibitors of $PLA_2$, more particularly cPLA$_2$. As such, the present invention provides novel substituted pyrimidines which have the general structure:

(I)

with the symbols R$^1$, R$^2$, R$^3$, R$^4$ and R$^5$ representing the groups provided in the detailed description below. These compounds have activity as inhibitors of phospholipase A$_2$, and in particular cytosolic phospholipase A$_2$.

In other aspects, this invention provides pharmaceutical compositions of the substituted pyrimidine compounds of formula I or a pharmaceutically acceptable salt thereof with a pharmaceutically acceptable carrier.

As described in detail below, the compounds of formula I are useful in the treatment of conditions associated with PLA$_2$-mediated conditions, such as inflammation and Alzheimer's disease. As such, the present invention provides a method of treating cPLA$_2$-dependent diseases. In this aspect, the method comprising administering to a subject having at least one of cPLA$_2$-mediated disease with an effective amount of a compound of formula I.

The compounds and pharmaceutical compositions of compounds of formula I are also useful for in vitro assays for PLA$_2$ inhibitors. As such, in another aspect, the present invention provides a method of inhibiting PLA$_2$ activity in vitro, comprising contacting a cell having PLA$_2$ activity with a compound of formula I and assaying the PLA$_2$ activity.

In another embodiment, the present invention provides the use for the manufacture of a medicament for the treatment of inhibiting PLA$_2$ activity and treating cPLA$_2$-dependent diseases. These and other aspects of the present invention will be described in detail hereinbelow.

BRIEF DESCRIPTION OF THE DRAWINGS

FIG. 1 (Panels A and B) provide synthesis schemes for the compounds of the present invention.

FIG. 2 (Panels A, B, C and D) provide synthesis schemes for the compounds of the present invention.

FIG. 3 (Panels A and B) provide synthesis schemes for the compounds of the present invention.

DETAILED DESCRIPTION OF THE INVENTION

I. Glossary

Abbreviations and Definitions

The term "active agent" is used herein to refer to an agent which inhibits PLA$_2$ activity. Active agents can be sold as commercial reagents for standardizing toxicological or pharmaceutical evaluations which employ neuron cultures or transgenic animals which exhibit neurodegenerative pathology. Some active agents will have therapeutic potential as drugs for human use such as in treating inflammation, neurodegenerative disorders or stroke patients. The active agents described herein are all substituted pyrimidines which selectively inhibit PLA$_2$. A selective inhibitor of PLA$_2$ produces a preferential inhibition of PLA$_2$ as compared to inhibition of other mammalian phospholipases, such that the concentration required to produce inhibition of 50% of PLA$_2$ catalytic activity is at least one order of magnitude lower than the concentration required to produce inhibition of 50% of the catalytic activity of phospholipases other than PLA$_2$. A selective inhibitor of cPLA$_2$ produces a preferential inhibition of cPLA$_2$ as compared to inhibition of other mammalian PLA$_2$ enzymes.

The term "PLA$_2$" as used herein refers to a naturally-occurring mammalian phospholipase A$_2$ polypeptide having enzymatic activity. These enzymes catalyze the hydrolysis of the 2-acyl ester bond of phosphoglycerides generating free fatty acids and lysophospholipids. Since the sn-2 position of phospholipids of mammalian cells is enriched with arachidonic acid, the precursor for eicosanoids, PLA$_2$ activity has important implications for the control of eicosanoid production. A paradigmatic PLA$_2$ can be considered to be human cPLA$_2$ substantially equivalent to that such as that described in U.S. Pat. Nos. 5,354,677 and 5,328,842; Clark et al. (1991) *Cell* 65: 1043, and Sharp et al. (1991) *J. Biol. Chem.* 266: 14850, or the cognate cPLA$_2$ enzyme in a non-human mammalian species. PLA$_2$ activity is present in a variety of cytosolic and extracellular PLA$_2$ polypeptide species. A preferred PLA$_2$ polypeptide of the invention is a cytosolic PLA$_2$, such as cPLA$_2$, and typically a calcium-activatable cPLA$_2$ which is activated (exhibits enhanced catalytic activity) by the presence of calcium ions (Ca$^{+2}$).

The term "cPLA$_2$-dependent disease" as used herein refers to a cPLA$_2$-mediated disease. These diseases are characterized in some instance by destructive cellular processes, membrane degradation, mitochondrial dysfunction; impaired ATP synthesis and impaired blood and oxygen delivery to tissues. These diseases include, but are not limited to, neurodegenerative diseases, cytokine-mediated conditions, conditions associated with metabolites of arachidonic acid and dysfunctions associated with inflammatory responses. (see, J. V. Bonventre (1997) *J. Lipid Mediators Cell Signalling*, 16: 199–208.)

The term "alkyl" refers to a branched, or straight chain group typically containing only carbon and hydrogen, and unless otherwise mentioned, contains one to twelve carbon atoms, such as C$_1$–C$_6$. This term is further exemplified by groups such as methyl, ethyl, n-propyl, isobutyl, t-butyl, pentyl, pivalyl and heptyl. Alkyl groups can either be unsubstituted or substituted with one or more substituents, e.g., halogen, alkoxy, alkylthio, trifluoromethyl, acyloxy, hydroxy, mercapto, carboxy, aryloxy, aryl, heteroaryl, heterocycle, amino, morpholino, piperidino, pyrrolidin-1-yl, piperazin-1-yl, or other functionality.

The term "lower alkyl" refers to a branched or straight chain monovalent alkyl radical of one to six carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, and hexyl.

The term "aryl" or "Ar" refers to a monovalent unsaturated aromatic carbocyclic group having a single ring (e.g., phenyl) or multiple rings either condensed rings (e.g., naphthyl or anthryl), linked covalently (e.g., biphenyl) or linked to a common group such as an ethylene or methylene moiety (e.g., diphenylmethyl). The aromatic rings can optionally be unsubstituted or substituted with, e.g., halogen, alkyl, alkoxy, alkylthio, trifluoromethyl, acyloxy, hydroxy, mercapto, carboxy, aryloxy, arylalkyl, heteroaryl, heterocycle, amino, morpholino, piperidino, pyrrolidin-1-yl, piperazin-1-yl, or other functionality. The term "heteroaryl" or "HetAr" is an aromatic heterocycle (e.g. pyridine, quinoline, quinoxaline, thiophene, furan, pyrrole and the like).

The term "alkoxy" refers to a group having the structure —O—R, where R is alkyl, as described above, which may be substituted with a non-interfering substituent.

As used herein, the term "halo," "halogen atom" or "halide" refers to fluoro, bromo, chloro and iodo substituents. As used herein, the term "amino" refers to a chemical functionality —$NR^aR^b$, where $R^a$ and $R^b$ are independently hydrogen, alkyl, or aryl.

The term "pharmaceutical agent or drug" as used herein refers to a chemical compound or composition capable of inducing a desired therapeutic effect when properly administered to a patient.

Other chemistry terms herein are used according to conventional usage in the art, as exemplified by *The McGraw-Hill Dictionary of Chemical Terms* (ed. Parker, S., 1985), McGraw-Hill, San Francisco, incorporated herein by reference).

II. Substituted Pyrimidines

A. Compounds

The present invention provides compounds which are useful for the inhibition of phospholipase $A_2$. In particular, the invention provides substituted pyrimidines having the formula:

(I)

In this formula, the symbol $R^1$ represents a $C_1$–$C_6$ alkyl, $C_1$–$C_6$ alkoxy or halogen atom. The symbol $R^2$ represents a phenyl group, substituted phenyl group, benzyl moiety, substituted benzyl moiety, $C_3$–$C_7$ cycloalkyl, or substituted $C_3$–$C_7$ cycloalkyl. The symbol $R^3$ represents a hydrogen or $C_1$–$C_6$ alkyl group. The symbol $R^4$ represents —H, —OH, —$N_3$ or —$NHCOCH_3$. The symbol $R^5$ represents H or alkyl, preferably H.

The compounds of formula I include pharmaceutically acceptable salts, which can be salts with cations. Cations with which the compounds of this invention can form salts include alkali metals, such as potassium and sodium or alkaline earth metals, such as calcium. Those skilled in the art will be aware of other salts which would be useful in the present invention.

In the above definition of the compound (I) according to the present invention, the lower alkyl group defined with respect to $R^1$ and $R^3$ is a straight chain or branched alkyl group having 1 to 6 carbon atoms. Methyl, ethyl, propyl and isopropyl groups are preferred.

The lower alkoxy group is one derived from the above-mentioned lower alkyl group having 1 to 6 carbon atoms and preferable examples thereof include methoxy, ethoxy, n-propoxy, isopropoxy and n-butoxy groups.

The unsubstituted cycloalkyl group defined with respect to $R^2$ includes cyclopropyl, cyclobutyl, cyclopentyl, cyclohexyl, cycloheptyl, cyclooctyl, cyclononyl, cyclodecyl, cyclododecyl and adamantyl groups. Preferably, the unsubstituted cycloalkyl group is a cyclopentyl group.

The $C_3$–$C_7$ substituted cycloalkyl group is a cycloalkyl group as described above which is either substituted with a lower alkyl group such as a methyl group, or a halogen atom. Further, cycloalkyl groups can substituted with one or more substituents, e.g., halogen, alkoxy, alkylthio, trifluoromethyl, acyloxy, hydroxy, mercapto, carboxy, aryloxy, heteroaryl, heterocycle, amino, morpholino, piperidino, pyrrolidin-1-yl, piperazin-1-yl, or other functionality.

Alternatively, when a cycloalkyl group is condensed with an aromatic ring such as a benzene ring or a heterocyclic ring such as a pyridine ring at adjacent carbon atoms constituting the cycloalkyl group it forms a substituted-aryl group or substituted heteroaryl group, respectively, represented by the formula:

The substituted or unsubstituted phenyl group defined with respect to $R^2$ is a phenyl ring which is substituted with a lower alkyl group such as a methyl, ethyl or isopropyl group, a halogen atom, or a lower alkoxy group such as a methoxy group. Still other substituents will include nitro, amino, alkylamino, dialkylamino, carboxyl, carbamoyl, $C_1$–$C_8$ acyl, sulfonyl, thiol, alkylthio and the like, and combinations thereof Preferably, the substituents are selected from a lower alkyl group such as a methyl or ethyl group, halogen atoms and lower alkoxy groups such as a methoxy and isopropoxy groups.

B. Methods of Preparation

The compounds of the present invention are readily prepared from commercially available starting materials via procedures and methods provided in the Examples below. Synthetic schemes which are useful for preparation of the compounds are provided as FIGS. 1–3.

Figure 1A:
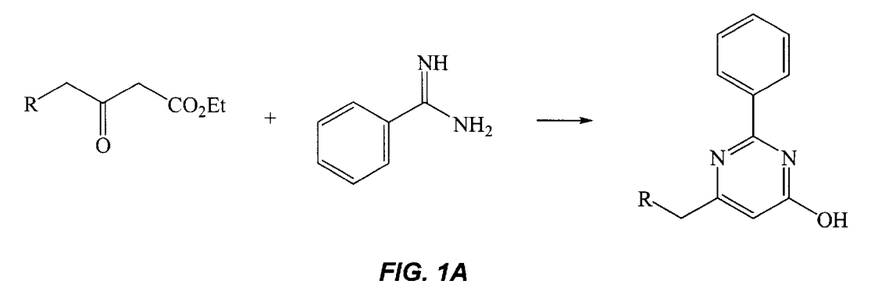
Figure 1B:
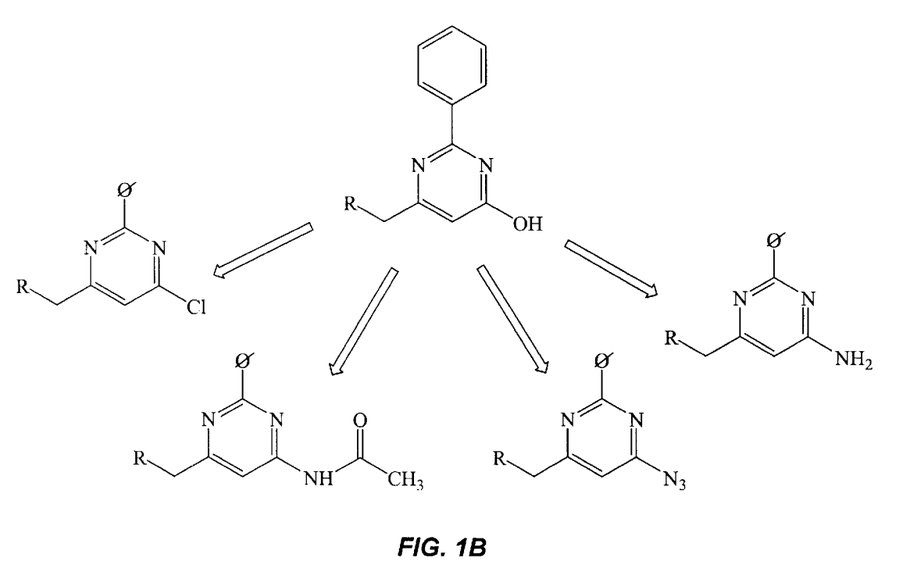

Briefly, the pyrimidine portion of the compounds can be constructed by combining a β-keto ester with a benzamidine as illustrated in FIG. 1A (using conditions described in Methods A and B, below). The resultant pyrimidine-4-ol can be further converted to 4-substituted pyrimidines (e.g., 4-chloro, 4-amino, 4-azido, 4-acetamido) or the hydroxyl group can be removed using literature procedures (see FIG. 1B, and Methods D–F below).

Construction of appropriate β-keto esters can be accomplished as outlined in FIG. 2. For example, carboxylation of a diphenylmethane (or substituted diphenylmethane) provides a diphenylacetic acid which can be converted to a β-keto ester (see FIG. 2A and procedures 4 and 5 in Section IIB, below). The diphenylmethanes are either commercially obtained, or prepared via methods outlined in FIG. 2B. Briefly, a benzaldehyde or substituted benzaldehyde can be treated with phenylmagnesium bromide (or an equivalent metallated aromatic species) to provide a benzhydrol group which can then be reduced (e.g., catalytic hydrogenation) to remove the benzylic hydroxyl thereby forming a substituted diphenylmethane.

Figure 2A:
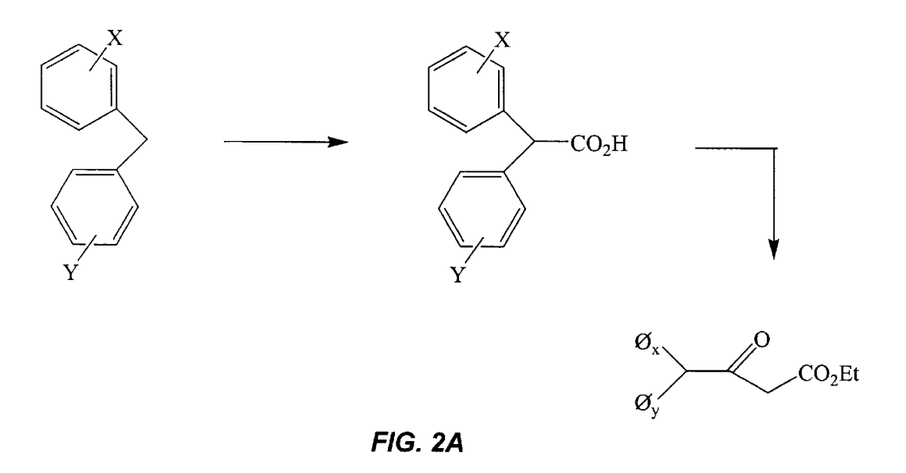
Figure 2B:
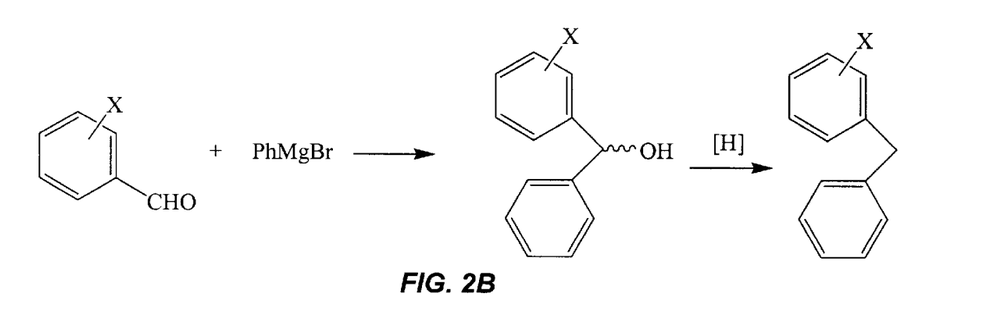
Figure 2C:
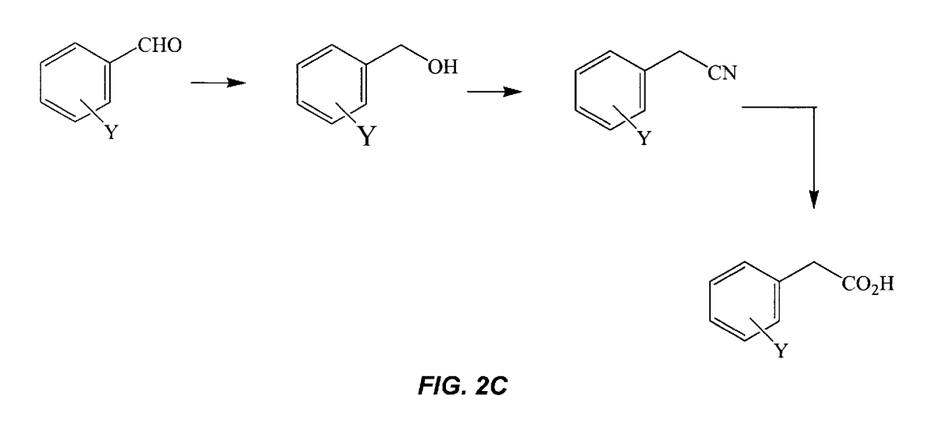
Figure 2D:
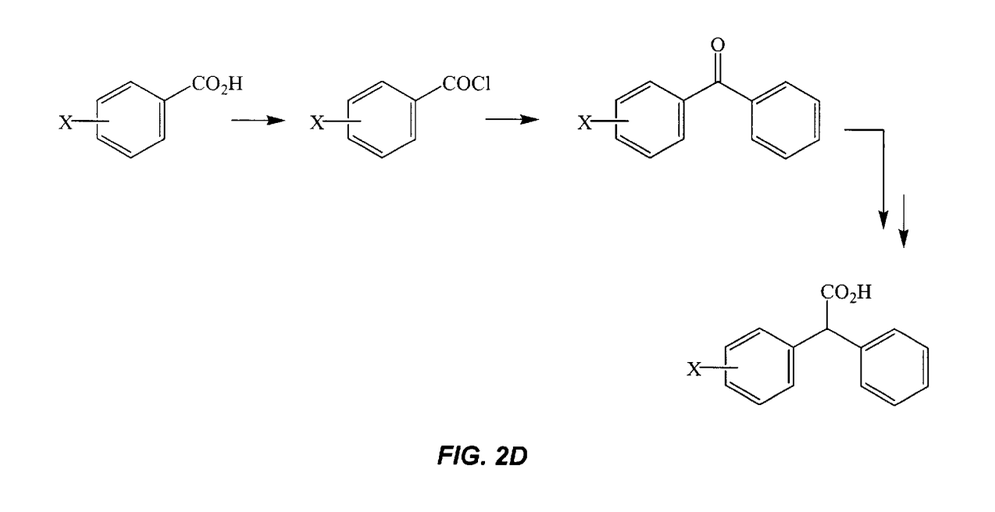

Other β-keto esters which are useful in the present invention can be prepared from substituted benzaldehydes (via substituted phenylacetic acids, see FIG. 2C) and from substituted benzoic acids (via substituted benzophenones, see FIG. 2D). As illustrated in FIG. 2C, a substituted benzaldehyde can be reduced to the corresponding benzyl alcohol, then converted first to a phenylacetonitrile, then to a phenylacetic acid. The substituted phenylacetic acid is then converted to a β-keto ester and used as described above. Procedures 5–8, in Section IIIB below, provide representative conditions of the processes illustrated in FIG. 2C. Conversion of a substituted benzoic acid to a substituted diphenylacetic acid is illustrated in FIG. 2D. Briefly, the starting acid is converted to an acid chloride which is used to acylate a second aromatic ring to provide a benzophenone. Conversion of the substituted benzophenone to a substituted diphenylacetic acid is accomplished using TosMIC to form a substituted diphenylacetonitrile which is hydrolyzed to the corresponding substituted diphenylacetic acid. Procedures 5 and 8–10 in Section IIIB below, provide representative conditions for the processes outlined in FIG. 2D.

Figure 3A:
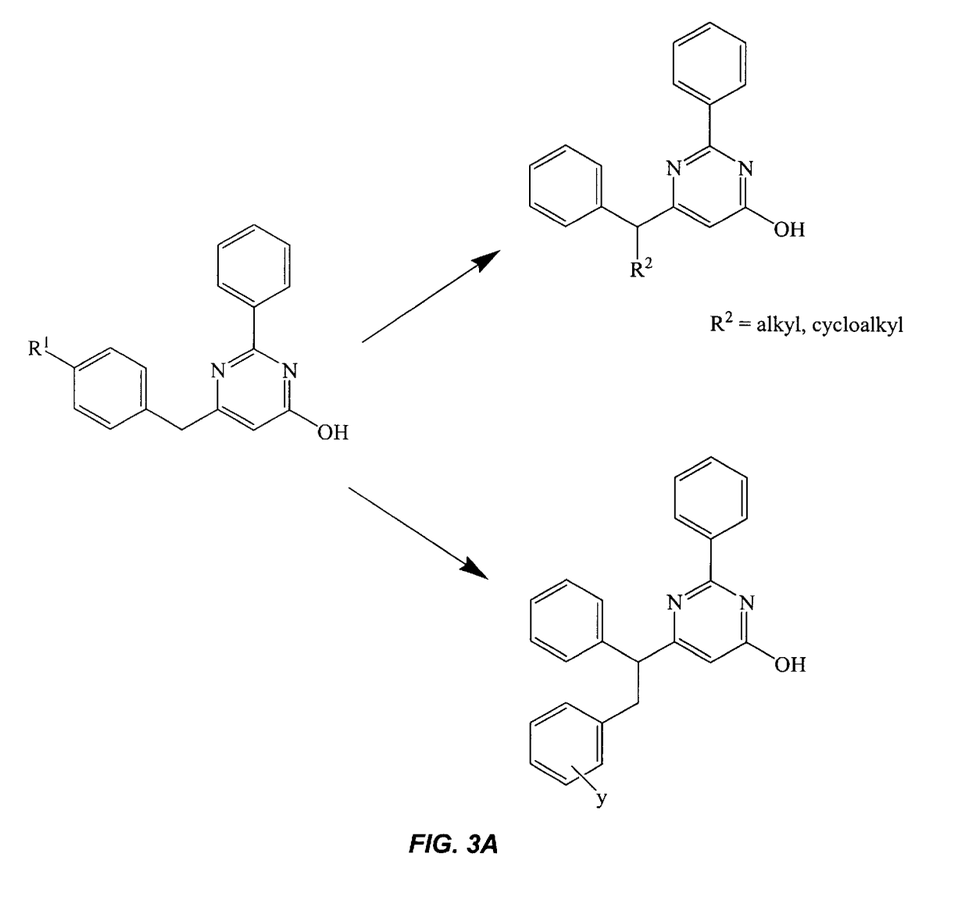

Some compounds of the present invention can be prepared by x-alkylation of pyrimidines, as illustrated in FIG. 3A. According to this scheme, a pyrimidine having a benzylic group at the 6-position can be metallated (e.g., using lithium diisopropylamide) and added to an alkyl halide or benzyl halide (e.g., methyl iodide, cyclopentylbromide or benzyl bromide) to provide the desired targets. Method C, below, provides representative conditions.

Figure 3B:
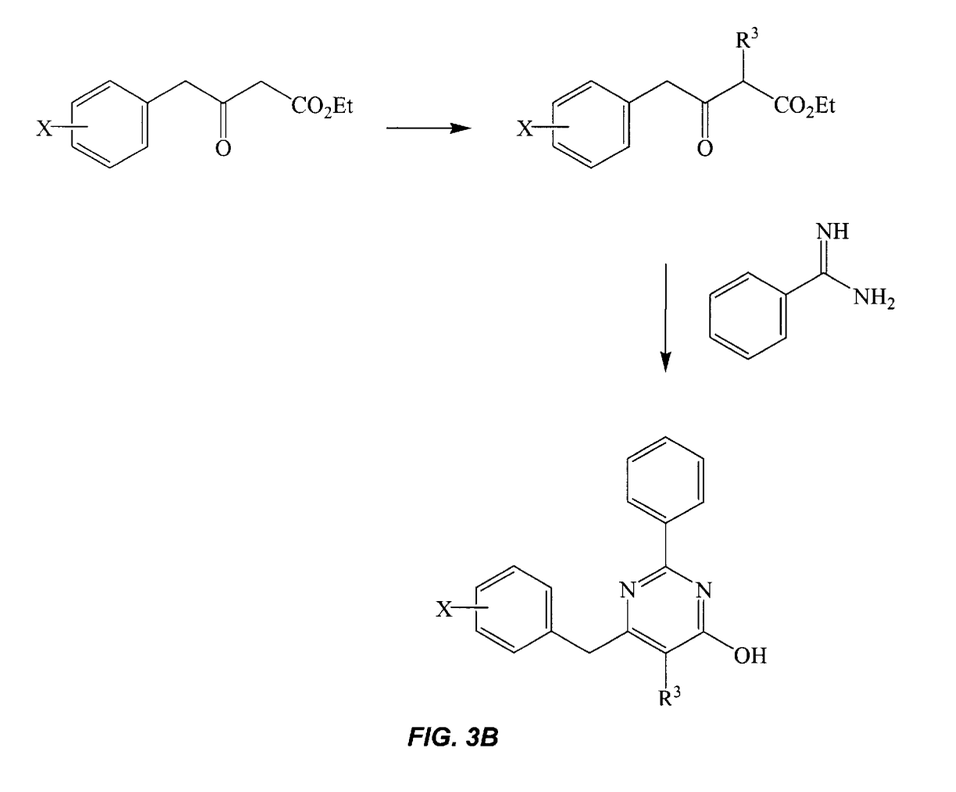

Compounds having alkyl groups at the 5-position of the pyrimidine ring (e.g., $R^3$ is $C_1$–$C_6$ alkyl) can be prepared by alkylating the intermediate β-keto ester as illustrated in FIG. 3B. While the process is illustrated for a β-keto ester derived from a substituted diphenylacetic acid, one of skill in the art will understand that the alkylation conditions can be used with essentially any of the β-keto esters described above.

Some of the compounds of the present invention contain one or more asymmetric centers and may thus give rise to diastereomers and optical isomers. The present invention is meant to include such isomers as well as their racemic and resolved, enantiomerically pure forms and pharmaceutically acceptable salts thereof Conditions for the separation of enantiomers are provided in Procedure 12 in Section IIIB below. However, equivalent methods known to those of skill in the art may also be employed.

Using the methods described above, and provided in detail below, representative compounds of formula I are set forth in Table I.

TABLE I

| Compound | $R^1$ | $R^2$ | $R^3$ | $R^4$ | $R^5$ |
|---|---|---|---|---|---|
| 1 | isobutyl | methyl | H | —$N_3$ | H |
| 2 | isobutyl | methyl | H | —NHCOCH$_3$ | H |
| 3 | isobutyl | benzyl | H | —OH | H |
| 4 | isopropyl | benzyl | H | —OH | H |
| 5 | isobutyl | phenyl | H | —OH | H |
| 6 | isopropyl | phenyl | H | —OH | H |
| 7 | —H | 4-tolyl | H | —OH | H |
| 8 | chloro | 4-chlorophenyl | H | —OH | H |
| 9 | —H | cyclopentyl | H | —OH | H |
| 10 | ethyl | phenyl | H | —OH | H |
| 11 | isopropoxy | phenyl | H | —OH | H |
| 12 | methoxy | phenyl | H | —OH | H |
| 13 | ethyl | phenyl | H | —H | H |
| 14 | ethoxy | phenyl | H | —OH | H |
| 15 | propyl | phenyl | H | —OH | H |
| 16 | methoxy | 4-methoxyphenyl | H | —OH | H |
| 17 | isobutyl | 2,4-difluorobenzyl | H | —OH | H |
| 18* | propyl | phenyl | H | —OH | H |
| 19* | propyl | phenyl | H | —OH | H |
| 20 | isobutyl | 2-bromophenyl | H | —OH | H |
| 21* | isopropoxy | phenyl | H | —OH | H |
| 22* | isopropoxy | phenyl | H | —OH | H |
| 23 | isopropyl | phenyl | CH$_3$ | —OH | H |
| 24 | butyl | phenyl | H | —OH | H |
| 25 | ethoxy | 4-ethoxyphenyl | H | —OH | H |

*indicate compounds with $IC_{50} < 100$ nM

C. Pharmaceutical Compositions

Active agents which inhibit $PLA_2$ can be used to retard or reduce neurodegeneration in vivo. Additionally, those agents which inhibit $PLA_2$ activity can be used for the treatment of other conditions mediated by $PLA_2$, as described previously. Thus, the present invention further comprises pharmaceutical compositions incorporating one or more of the substituted pyrimidines described herein in a pharmaceutically acceptable carrier. Such pharmaceutical compositions should contain a therapeutic or prophylactic amount of at least one substituted pyrimidine. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, *Remington's Pharmaceutical Sciences*, Mack Publishing Company, Easton, Pa., 16th Ed., 1982,. the disclosure of which is incorporated herein by reference.

The pharmaceutical compositions just described are suitable for systemic administration to the host, including both parenteral, topical, and oral administration, including intracranial administration. Thus, the present invention provides compositions for administration to a host, where the compositions comprise a pharmaceutically acceptable solution of the identified inhibitory compound in an acceptable carrier, as described above.

Compositions containing the present inhibitors (or active agents) can be administered for prophylactic and/or therapeutic treatments of neurodegenerative disease. In therapeutic application, compositions are administered to a patient already affected by the particular neurodegenerative disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 10 g of $PLA_2$ inhibitor per dose, with dosages of from 10 mg to 2000 mg per patient being more commonly used. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences. Further methods of determining an effective dose range utilize data obtained from the in vitro assays described herein. An effective inhibitory concentration determined in such an assay is extrapolated to estimate an effective cellular concentration in vivo, according to methods known in the art.

The compositions for parenteral administration will commonly comprise a solution of an active agent or a cocktail thereof dissolved in an acceptable carrier, preferably an aqueous carrier or organic solvent (e.g., DMSO, solvated PEG, etc.). Since many of the active agents of the invention can be lipophilic or latentiated, it is preferable to include in the carrier a hydrophobic base (e.g., polyethylene glycol, Tween 20). A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the active agent in these formulations can vary widely, i.e., from less than about 1 nM, usually at least about 0.1 mM to as much as 100 mM and will be selected primarily based on fluid volumes, viscosities, etc., in accordance with the particular mode of administration selected. Most usually, the active agent is present at a concentration of 0.1 mM to 5 M. For example, a typical formulation for intravenous or intracranial injection comprises a sterile solution of an active agent at a concentration of 1–500 mM in Ringer's solution. The generally hydrophobic nature of some of the active agents indicates that a hydrophobic vehicle may be used, or that an aqueous vehicle comprising a detergent or other lipophilic agent (e.g., Tween, NP-40, PEG); alternatively, the active agents may be administered as a suspension in an aqueous carrier, or as an emulsion.

Thus, a typical pharmaceutical composition for intramuscular injection could be made up to contain 10 mL sterile buffered water, and about 1–1000 mg of active agent. A typical composition for intravenous infusion can be made up to contain 250 mL of sterile Ringer's solution, and about 100–5000 mg of active agent. Lipophilic agents may be included in formulations. Actual methods for preparing parenterally administrable compositions will be known or apparent to those skilled in the art and are described in more detail in, for example, Remington's Pharmaceutical Science, 15th Ed., Mack Publishing Company, Easton, Pennsylvania (1980), which is incorporated herein by reference.

III. Examples

A. Assays for Determining Biological Activity

1. General

Several $PLA_2$ assays have previously been described. For instance, U.S. Pat. No. 5,464,754 describes a non-radioactive, spectrophotometric, microtiter plate assay for human $cPLA_2$. In addition, Reynolds et al. (1994) *Anal. Biochem.* 217: 25 describe a convenient microtiter plate assay for $cPLA_2$. Moreover, Currie et al. (1994) *Biochem. J.* 304: 923, describe a $cPLA_2$ assay for assaying $cPLA_2$ activity from activated whole cells. This assay can be adapted for assay of related $PLA_2$ activity, whether from $cPLA_2$ or other $PLA_2$ enzymes having similar catalytic activities.

2. Inhibition of Phospholipase $A_2$

The $PLA_2$ inhibitory properties of the compounds of the present invention were evaluated using the following assays. Inhibition of release of [$^{14}C$]-AA from phosphatidylcholine was measured according to standard methods. Human U937 cells were cultured in RPMI 1640 medium supplemented with 10% fetal bovine serum, penicillin, L-glutamine, and HEPES buffer. Cells were harvested and washed 3 times with extraction buffer (140 mM NaCl—5 mM KCl—2 mM EDTA—25 mM Tris pH 7.4) and resuspended at $1 \times 10^8$ cells/mL containing 100 $\mu$M leupeptin—50 $\mu$M pepstatin—1 mM PMSF. Cells were placed in a $N_2$ cavitation bomb and put under pressure at 600 psi or maximum pressure for 20 minutes at 4° C. Cells were then released. The suspension was collected and centrifuged at 100,000 g for 60 minutes at 4° C. The resulting supernatant was collected and filtered through a 0.22 $\mu$m filter. Extract was then diluted to 50% glycerol and stored at −20° C.

For the preparation of substrate, 20 nmol of phosphatidylcholine-$\alpha$-1-palmitoyl-2-arachidonyl-1-[$^{14}C$] and 10 nmol 1,2-dioleyl-glycerol were mixed together and dried under a $N_2$ stream. A solution of 1 mL of 150 mM NaCl—50 mM HEPES pH 7.5 was added to the mixture. To reconstitute liposomes, the mixture was sonicated using a Branson 450 sonifier for 2 minutes at 50% duty cycle output level 3 on ice. After sonification, 40 $\mu$L of a 100 mg/mL BSA solution was added per mL.

The compounds were first dissolved in DMSO at 2 mM and serially diluted in DMSO by a factor of five for a total of 5 concentrations. These dilutions were further dissolved 60 fold in reaction buffer (150 mM NaCl—50 mM HEPES pH 7.5—1 mM $CaCl_2$—1 mM 2-ME) containing approximately 5% of the U937 cytosolic extract to make up the preincubation mixture which was then incubated for 20 minutes at 37° C. Vehicle control using only DMSO with no compound was also made. To 30 $\mu$L of this Extract/compound mixture was added 10 $\mu$L of substrate. The 40 $\mu$L reaction mixture was incubated for 15 minutes at 37° C., and the reaction was stopped by adding 400 $\mu$L Dole's reagent [2-propanol/heptane/0.5 M $H_2SO_4$ (40:10:1) 10 $\mu$g/mL stearic acid]. This was followed by the addition of 240 $\mu$L heptane and 200 $\mu$L water. 280 $\mu$L of the top heptane layer was transferred to a tube containing 60 mL silica gel with 200 $\mu$L heptane and mixed vigorously. Silica gel was then centrifuged at 1000 g for 1 minute. 400 $\mu$L of liquid was transferred to scintillation vial along with 4 mL of Beckman Ready Safe scintillation cocktail and mixed. Radioactivity was determined in a Beckman scintillation counter.

B. Synthesis of Representative Compounds

1. General Methods and Procedures

All operations were carried out at room or ambient temperature, that is, at a temperature in the range of 18–25°

C.; evaporation of solvent was carried out using a rotary evaporator under reduced pressure (600–4000 pascals: 4.5–30 mmHg) with a bath temperature in the range of up to 60C; the course of the reaction was followed by thin layer chromatography (TLC) and reaction times are given for illustration only; melting points given are uncorrected and are obtained for materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data yields are given for illustration only; when given, NMR data is in the form of delta ($\delta$) values for major diagnostic protons, given in parts per million (ppm) relative to tetramethylsilane (TMS) as internal standard, determined at 300 MHz using the indicated solvent; conventional abbreviations used for signal shape are: s, singlet; d, doublet; t, triplet; m, multiplet; br, broad; etc.: in addition chemical symbols have their usual meanings; the following abbreviations have also been used v (volume), w (weight), mp (melting point), L (liter(s)), mL (milliliters), g (gram(s)), mg (milligram(s)), mmol (millimoles), eq (equivalent(s)).

The following abbreviations have the indicated meanings: $Et_3N$, triethylamine; Ac, acetyl; DMF, N,N-dimethylformamide; Ph, phenyl; r.t., room temperature; and TLC, thin layer chromatography.

2. Preparation of benzhydrols

4-Isopropylbenzaldehyde (1.0 equiv.) was dissolved in THF and cooled in an ice bath. Phenylmagnesium bromide (Aldrich, 3.0 M in ether, 1.1 equiv.) was added via syringe and the mixture was stirred for 30 min. The reaction was quenched by addition of satd aq $NH_4Cl$ and the mixture was extracted with ether (2×100 mL). The combined extracts were dried ($Na_2SO_4$), filtered and evaporated in vacuo to give a residue which was recrystallized or used crude in the next procedure.

3. Reduction to Diphenylmethane

The benzhydrol was dissolved in EtOAC and 10% Pd/C was added. The mixture was hydrogenated at ca. 40 psi $H_2$ for 48 h. The solution was filtered through a pad of Celite to remove catalyst and evaporated in vacuo to give a residue which was purified by silica gel chromatography to give the diphenylmethane.

4. Carboxylation of Diarylmethane

The diaryl methane (5 mmol) was dissolved in THF (10 mL) and cooled in an ice bath. Lithium diisopropylamide (6 mmol, 3 mL of 2M LDA in heptane) was added via syringe and the mixture was warmed to room temperature and stirred for 20 min-2 h until the deep red anion formed. The mixture was then poured onto freshly crushed dry ice (large excess) and allowed to warm to room temp. The mixture was slurried in water (50 mL) and extracted with ether (2×30 mL) to remove unreacted starting material. The aqueous layer is then made acidic with 1 N HCl and extracted with ether (2×30 mL). The combined ether extracts were dried ($MgSO_4$), filtered and evaporated in vacuo to give the carboxylic acid.

Alternatively, the diarylmethane (5 mmol) was dissolved in THF (10 mL) and cooled in an ice bath. One drop of diisopropylamine was added, and then n-Butyllithium (5.1 mmol, 3.2 mL of 1.6 M LDA in hexane) was added via syringe and the mixture was and stirred for 20 min-2 h until the deep red anion forms. The mixture was then poured onto freshly crushed dry ice (large excess) and allowed to warm to room temp. The mixture was slurried in water (50 mL) and extracted with ether (2×30 mL) to remove unreacted starting material. The aqueous layer is then made acidic with 1 N HCl and extracted with ether (2×30 mL). The combined ether extracts were dried ($MgSO_4$), filtered and evaporated in vacuo to give the carboxylic acid.

5. Preparation of $\beta$-ketoesters

The carboxylic acid was dissolved in THF (ca. 2 mL/mmol acid) and carbonyl diimidazole (1.2 equiv) was added and the mixture was stirred at room temp for 30–60 min. Meanwhile, ethyl hydrogen malonate (1.5 equiv) was dissolved in THF (ca. 3 mL/mmol above acid) and cooled to −40° C. Isopropyl magnesium chloride (2.0 M in THF, 3 equiv) was added via syringe and the mixture was allowed to warm to −20° C. over 30–60 min. The resulting slightly milky solution was recooled to −40° C. and the acyl imidazole solution (above) was added dropwise via cannula. The mixture was allowed to slowly warm to room temp (4 h or overnight) before addition of IN HCl (ca. 6 equiv). After $CO_2$ evolution ceases, the mixture was diluted with water and extracted with EtOAc. The combined organic extracts were washed with ½ satd aq $NaHCO_3$, dried, and evaporated in vacuo to yield give a residue which was purified by silica gel chromatography to yield the $\beta$-keto ester.

6. Reduction of Isobutylbenzaldehyde

Lithium aluminum hydride (586 mg, 15.4 mmol) was slurried in diethyl ether (50 mL) and cooled in an ice bath. A solution of 4-isobutylbenzaldehyde (5.00 g, 30.9 mmol) in diethyl ether (30 mL) was added dropwise over 10 min and the mixture was stirred for 30 min before successive addition of water (0.6 mL), 15% aq NaOH (0.6 mL), and water (1.8 mL). The resulting precipitate was removed via filtration and the filtrate was dried ($MgSO_4$), filtered, and evaporated in vacuo to give 4-isobutylbenzyl alcohol (4.78 g, 94%). $^1$H NMR ($CDCl_3$) 7.28 (d, 2H), 7.13 (d, 2H), 4.63 (s, 2H), 2.45 (d, 2H), 1.85 (m, 1H), 0.90 (d, 6H).

7. Conversion to Nitrile

4-Isobutylbenzyl alcohol (4.77 g, 29.0 mmol) was dissolved in diethyl ether and phosphorous tribromide (11.79 g, 43.1 mmol) was added and the mixture was heated to reflux for 3 h. The mixture was cooled to 0° C. and carefully poured onto ice. The layers were separated and the aqueous layer was extracted with diethyl ether (50 mL). The combined organic layers were dried ($Na_2SO_4$), filtered and evaporated in vacuo to give the crude benzyl bromide which was used directly in the next step. $^1$H NMR ($CDCl_3$) 7.31 (d, 2H), 7.12 (d, 2H), 4.49 (s, 2H), 2.46 (d, 2H), 1.85 (m, 1H), 0.89 (d,6H), The benzyl bromide (29 mmol) was dissolved in EtOH (105 mL) and water (45 mL) and potassium cyanide (3.40 g, 52.3 mmol) was added and the mixture was heated to reflux for 1 h. The mixture was cooled to room temp and the volatiles were removed in vacuo. The residue was diluted with water (300 mL) and the mixture was extracted with diethyl ether (2×100 mL). The combined organic extracts were dried ($Na_2SO_4$), filtered and evaporated in vacuo to give the nitrile (4.99 g, 99%). $^1$H NMR ($CDCl_3$) 7.24 (d, 2H), 7.15 (d, 2H), 3.72 (s, 2H), 2.46 (d, 2H), 1.85 (m, 1H), 0.90 (d, 6H).

8. Hydrolysis of Nitrile to Carboxylic Acid

4-Isobutylphenylacetonitrile (4.99 g, 28.8 mmol) was dissolved in glacial acetic acid (20 mL) and 8N HCl (20 mL) was added. The mixture was heated to reflux for 48 h. The mixture was cooled to room temp and the volatiles were removed in vacuo. The residue was diluted with water (50 mL) and extracted with diethyl ether (2×50 mL). The combined organic extracts were washed with water (50 mL), dried ($Na_2SO_4$), filtered and dried in vacuo to give the carboxylic acid (4.99 g, 90%). $^1$H NMR ($CDCl_3$) 7.20–7.05 (m, 4H), 3.61 (s, 2H), 2.45 (d, 2H), 1.83 (m, 1H), 0.90 (d, 6H).

9. Preparation of Substituted Benzophenones

A solution of 4-isobutylbenzoic acid (5.00 g, 28.0 mmol) in $CH_2Cl_2$ was cooled in an ice bath and treated with oxalyl chloride (5 mL) and DMF (1 drop). The mixture was warmed to room temp and stirred 1 h. The volatiles were removed in vacuo to give the crude acid chloride which as dissolved in benzene (50 mL). Aluminum chloride (4.49 g, 33.3 mmol) was added and the mixture was heated to reflux for 3.5 h. The mixture was cooled to room temp and then poured onto ice (ca. 100 g). The mixture was extracted with EtOAc (3×100 mL) and the combined organic extracts were washed with ½ satd aqueous $NaHCO_3$ (100 mL), dried ($Na_2SO_4$), filtered and evaporated in vacuo. The resulting residue was purified by silica gel chromatography (elute with 10:1 hexane/EtOAc) to give 4-isobutylbenzophenone (5.48 g, 81%). $^1$H NMR ($CDCl_3$) 7.75 (m, 4H), 7.53 (d, 1H), 7.47 (t, 2H), 7.23 (d, 2H), 2.53 (d, 2H), 1.91 (m, 1H), 0.92 (d, 6H).

10. TosMIC Reaction

A solution of tosylmethylisocyanide (2.13 g, 10.9 mmol) in DMSO (13 mL) was cooled in an ice bath and potassium tert-butoxide (3.30 g, 29.4 mmol) was added in one portion. The mixture was stirred for 5 min before addition of MeOH (0.42 mL) and 4-isobutylbenzophenone (2.00 g, 8.39 mmol). The mixture was warmed to room temp and stirred 18 h and then diluted with water (25 mL). The mixture was made acidic with 1H HCl (35 mL) and extracted with a 1:1 mixture of hexane/diethyl ether (3×100 mL). The combined organic extracts were washed with brine (100 mL), dried ($Na_2SO_4$), filtered and evaporated in vacuo to give a residue which was purified by silica gel chromatography (eluted with 6:1 Hexane/EtOAc) to give the nitrile (1.62 g, 78%). $^1$H NMR ($CDCl_3$) 7.80–7.20 (9H), 5.05 (s, 1H), 2.43 (d, 2H), 1.85 (m, 1H), 0.90 (d, 6H).

11. Alkylation of β-keto Ester

The β-ketoester (1.00 g, 3.08 mmol) was dissolved in THF and cooled in a dry ice/iPrOH bath. Potassium tert-butoxide (518 mg, 4.62 mmol) was added, followed by iodomethane (656 mg, 4.62 mmol). The mixture was warmed to room temp and stirred 48 h before addition of saturated aqueous $NH_4Cl$. The mixture was extracted with EtOAc. The EtOAc extracts were dried ($Na_2SO_4$), filtered and evaporated in vacuo to give the product.

12. HPLC Separation of Enantiomers

The enantiomers of the pyrimidines were separated via HPLC using a chiral column. A Chiracel OD-H chiral column (Diacel 588-705-50926) was used with an elution rate of 5 mL/min (elution program of 50% iPrOH/50% hexane for 25 min; then 40% iPrOH/60% hexane for 40 min). The pooled fractions were evaporated in vacuo to provide the separated isomers.

IV. METHOD OF SYNTHESIS

A. Pyrimidine Preparation Using Sodium Methoxide

The β-keto ester (1.0 equiv) was dissolved in MeOH (5 mL) and benzamidine hydrochloride (2 equiv.) was added and the mixture was cooled in an ice bath. Sodium methoxide (0.5 M in MeOH (Aldrich), 2 equiv.) was added and the mixture was warmed to room temperature and stirred for 48 h. The mixture was diluted with ½ saturated aqueous $NH_4Cl$ (50 mL) and extracted with EtOAc (3×30 mL). The combined extracts were washed with 0.2 N citric acid (30 mL) and ½ saturated solution of $NaHCO_3$ (30 mL), dried ($NaSO_4$), filtered and evaporated in vacuo to give a residue which was purified by silica gel chromatography to give the pyrimidine.

B. Pyrimidine Preparation Using Potassium Carbonate

The β-keto ester (1 equiv.) was dissolved in THF (6 mL) and water (3 mL) and benzamidine hydrochloride (1.5 equiv.) and potassium carbonate (1.5 equiv.) were added and the mixture was stirred for 24 h. The mixture was diluted with water (50 mL) and extracted with EtOAc (3×30 mL). The combined extracts were washed with 0.2 N citric acid (30 mL) and ½ satd aq $NaHCO_3$ (30 mL), dried ($NaSO_4$), filtered and evaporated in vacuo to give a residue which was purified by silica gel chromatography to give the pyrimidine.

C. α-Alkylation of Pyrimidine

The pyrimidine (1.0 equiv.) was dissolved in THF (3 mL) and cooled in a dry ice/iPrOH bath. Lithium diisopropylamide (Aldrich, 0.5 M in THF, 3.5 equiv.) was added via syringe and the mixture was stirred for 20 min before addition of neat alkyl halide (2.0 equiv.) the mixture was stirred for an additional 10 min before addition of satd aq $NH_4Cl$ (2 mL). The mixture was allowed to warm to room temp and was diluted with water (30 mL). The mixture was extracted with EtOAc (2×30 mL) and the combined organic extracts were dried ($Na_2SO_4$), filtered and evaporated in vacuo to give a residue which was purified by silica gel chromatography to yield the alkylated pyrimidine.

D. Modification of 4-Position with Azide

The 4-hydroxy pyrimidine was slurried in $POCl_3$ and heated to reflux for 1 h. The mixture was cooled to room temp and poured onto a mixture of ice/water. The pH was adjusted to neutral with concentrated aqueous $NH_4OH$ and the mixture was extracted with EtOAc (2×50 mL). The combined organic extracts were dried ($Na_2SO_4$), filtered and evaporated in vacuo to give the intermediate 4-chloropyrimidine.

The 4-chloropyrimidine was dissolved in DMF and treated with sodium cyanide and potassium carbonate. The reaction mixture was heated to 100° C. Reaction worked-up between ethyl acetate and $NaHCO_3$. The residue is purified by preparative tlc to yield desired product.

E. Modification of 4-Position as Acetamide

The 4-chloropyrimdine from method D was dissolved in MeOH (15 mL) in and the mixture was saturated with $NH_3$ gas. The mixture was heated in a sealed tube for 72 h. The volatiles were removed in vacuo and the residue was purified by silica gel chromatography (elute with 1% MeOH in $CH_2Cl_2$) to give the 4-aminopyrimidine.

The 4-aminopyrimidine (1.0 equiv.) was dissolved in THF and acetic anhydride (5 equiv.) and triethylamine (1.5 equiv.) were added and the mixture was stirred at room temperature. The volatiles were removed in vacuo and the residue purified by preparative silica gel TLC to give the 4-acetamidopyrimidine.

F. Modification of 4-Position as a Hydrogen.

The 4-chloropyrimidine (1.0 equiv) from method D was dissolved in ethyl acetate (2 mL). Potassium carbonate (1.0 equiv) was added along with 10% palladium on carbon. The mixture as hydrogenated for 48 h at 15–20 psi $H_2$ pressure. The mixture was filtered through a pad of diatomaceous earth and the solvent evaporated in vacuo. The residue was purified by preparative silica gel chromatography to give the pyrimidine.

EXAMPLE 1

6-(1-(4-Isobutyl)phenyl)ethyl-2-phenyl-4-azido-pyrimidine, 1

Ibuprofen was transformed to a β-keto ester using procedure 4, then converted to a pyrimidine by Method B. The pyrimidine thus obtained was converted to Compound 1 using Method D. Purification was carried out using preparative TLC to provide the title compound as an oil. $^1$H-NMR (CDCl$_3$) δ 8.2 (m, 1H); 7.6 (m, 2H); 7.5 (m, 1H); 7.3 (m, 2H); 3.8 (m, 1H); 3.0 (M, 1H); 1.6 (m,6H)

EXAMPLE 2

6-(1-(4-Isobutyl)phenyl)ethyl-2-phenyl-4-acetamido-pyrimidine, 2

Compound 2 was prepared from 4-chloropyrimidine by Method E. Purification was accomplished using column chromatography to provide the title compound as a solid (mp 75–85° C., dec) $^1$H-NMR (CDCl$_3$) 6 8.62 (s, 1H); 8.4 (m, 2H); 8.0 (s, 1H); 7.5 (m, 3H,):7.4 (d, 2H); 7.1 (d, 2H); 4.3 (m, 1H); 2.5 (d, 2H); 2.1 (s, 3H); 1.9 (m, 1H); 1.8 (d, 3H); 0.9 (d, 6H). $^{13}$C-NMR (CDCl$_3$) δ 176.3; 170.3; 164.2; 158.3; 141.5; 140.7; 138.2; 131.3; 129.9; 129.1; 128.8; 128.1; 106.4; 47.9; 45.6; 30.8;25.3; 23.0; 21.0.

EXAMPLE 3

6-(1-(4-isobutyl)phenyl-2-phenyl)ethyl-2-phenyl-pyrimidine-4-ol, 3

Compound 3 was prepared by alkylation of the unsubstituted pyrimidine using Method C. Purification was accomplished using flash chromatography and preparative TLC to provide the title compound. $^1$H-NMR (CDCl$_3$) δ 8.23 (m, 2H), 7.53 (m, 3H), 7.32 (d, J=8.0 Hz, 2H), 7.21–7.05 (7H), 6.22 (s, 1H), 407 (m, 1H), 3.66 (dd, J=8.6, 13.5 Hz, 1H), 3.25 (dd, J=6.5, 13.5 Hz, 1H), 2.42 (d, J=7.2 Hz, 2H), 1.82 (m, 1H), 0.87 (d, J=6.6 Hz, 6H). $^{13}$C-NMR (CDCl$_3$) δ 170.3, 165.4, 156.2, 140.3, 139.9, 138.9, 132.3, 131.9, 129.2, 129.0, 128.9, 128.2, 127.9, 127.8, 126.0, 111.0, 54.8, 45.0, 40.3, 30.2, 22.4.

EXAMPLE 4

6-(1-(4-Isopropyl)phenyl-2-phenyl)ethyl-2-phenyl-pyrimidine-4-ol, 4

Compound 4 was prepared similarly Compound 3. Purification was accomplished using column chromatography to provide the title compound as a solid (mp 152–154° C., dec). $^1$H-NMR (CDCl$_3$) δ 8.2 (m, 2H); 7.5 (m, 3H); 7.4 (d, 2H); 7.2–7.0 (m, 7H,); 6.2 (s, 1H); 4.1 (m, 1H); 3.7 (m, 1H); 3.2 (m, 1H); 2.8 (m, 1H); 1.2 (d, 6H). $^{13}$C-NMR (CDCl$_3$) δ 170.9; 166.3; 156.9; 148.1; 140.6; 139.7; 132.9; 135.2; 129.6; 129.5; 128.9; 128.7; 128.5; 127.2; 126.7; 111.7; 55.4; 40.9; 34.3; 24.6.

EXAMPLE 5

6-(((4-Isobutyl)phenyl,phenyl))methyl-2-phenyl-pyrimidine-4-ol, 5

Compound 5 was prepared from 4-isobutylbenzaldehyde by the procedures 5–9 followed by Method A to prepare the final product. Purification was accomplished using flash chromatography to provide the title compound. $^1$H-NMR (CDCl$_3$) δ 8.14 (m, 2H), 7.49 (m, 3H), 7.28 (m, 6H), 7.14 (m, 4H), 6.23 (s, 1H0, 5.41 (3, 1H), 2.46 (d, J=7.2 Hz, 2H), 1.86 (m, 1H), 0.91 (d, J=6.6 Hz, 6H). $^{13}$C-NMR (CDCl$_3$) δ 171.0, 165.8, 156.8, 141.4, 140.4, 138.3, 132.1, 132.0, 129.4, 129.3, 129.1, 128.9, 128.5, 127.9, 126.8, 112.4, 58.5, 44.9, 30.1, 22.3.

EXAMPLE 6

6-((4-Isopropyl)phenylphenyl)methyl-2-phenyl-pyrimidine-4-ol, 6

Compound 6 was prepared using synthesis described for the Compound 5 using 4-isopropylbenzaldehyde in procedure 5. Purification was accomplished using column chromatography to provide the title compound as a solid (mp 106–108° C.). $^1$H-NMR (CDCl$_3$) δ 8.15 (m, 2H); 7.45 (m, 3H); 7.3–7.1 (m, 9H); 6.3 (s, 1H); 5.4 (s, 1H); 2.9 (m, 1H); 1.2 (d, 6H). $^{13}$C-NMR (CDCl$_3$) δ 171.0; 165.9; 156.6; 147.5; 141.5; 138.2; 132.1; 132.0; 129.5; 129.3; 128.9; 128.5; 128.0; 126.8; 126.6; 112.4; 58.5, 33.6; 23.9.

EXAMPLE 7

6-((4-Methyl)phenyl,phenyl)methyl-2-phenyl-pyrimidine-4-ol, 7

Compound 7 was prepared using the synthetic route for Compound 6 using 4-methylbenzaldehyde in procedure 5. Purification was accomplished using column chromatography to provide the title compound as a solid (mp 210–214° C.). $^1$H-NMR (CDCl$_3$) δ 8.1 (m, 2H); 7.5 (m, 3H); 7.3–7.2 (m, 5H); 7.1 (s, 4H); 6.2(s, 1H), 5.4 (s, 1H); 2.3 (s,3H). $^{13}$C-NMR (CDCl$_3$) δ 170.9; 165.6; 156.5; 141.4; 138.2; 136.6; 132.1; 132.0; 129.4; 129.32; 129.29; 129.0; 128.5; 127.9; 126.9; 112.5; 58.4; 20.9. Mass spec (MH$^+$ 353). Analysis for C$_{24}$H$_{20}$N$_2$O; calculated, C 81.79, H 5.72, N 7.95; found C 81.43, H 5.91, N 7.75.

EXAMPLE 8

6-(bis-(4-Chloro)phenyl))methyl-2-phenyl-pyrimidine-4-ol, 8

4,4'-Dichlorophenyl acetic acid was converted to a β-ketoester using procedure 4. Compound 8 was then prepared using Method A. Purification was carried out using preparative TLC to provide the title compound as a solid (mp 245–246° C.). $^1$H-NMR (CDCl$_3$) δ 8.2 (m, 1H); 7.6 (m, 2H); 7.5 (m, 1H); 7.3 (m, 2H); 3.8 (m, 1H); 3.0 (m, 1H); 3.0 (m, 1H); 1.6 (m, 6H). $^{13}$C-NMR (CDCl$_3$) δ 173.3, 171.2, 165.8, 156.4, 141.3, 138.6, 132.2, 132.0, 129.0, 128.6, 127.6, 112.3. Mass spec (MH$^+$ 408, 409).

EXAMPLE 9

6-(1-Phenyl-1-cycloheptyl)methyl-2-phenyl-pyrimidine-4-ol, 9

Compound 9 was prepared in manner similar to that employed for compound 8, except that 1-cyclohepentyl-phenylacetic acid was used in place of the starting acid for compound 8. Purification was carried out using preparative TLC to provide the title compound as a solid (mp 212.5° C.). $^1$H-NMR (CDCl$_3$) δ 8.2 (m, 1H; 7.6 (m, 2H); 7.5 (m, 1H); 7.3 (m, 2H); 3.8 (m, 1H); 3.0 (m, 1H); 1.6 (m, 6H). $^{13}$C-NMR (CDCl$_3$) δ 166.9, 161.2, 151.9, 137.8, 127.9, 127.5, 124.5, 124.1, 123.8, 123.4, 122.3, 106, 55.5, 38.8, 27.1, 27, 20.7, 20.5. Mass spec (MH$^+$ 331).

EXAMPLE 10

6-((2-Ethyl)phenyl,phenyl)methyl-2-phenyl-pyrimidine-4-o, 10

Prepared as in example 6 using 4-ethylbenzaldehyde in procedure 5. Purification was accomplished using column chromatography to provide the title compound as a solid (mp 189–191° C.). $^1$H-NMR (CDCl$_3$) δ 8.1 (m, 2H); 7.5 (m, 3H); 7.3–7–2 (m, 9H); 6.2 (s, 1H); 5.4 (s, 1H); 2.6 (m, 2H); 1.2 (t, 3H). $^{13}$C-NMR (CDCl$_3$) δ 170.6; 165.8; 156.5; 142.9; 141.4; 138.4; 132.1; 132.0; 129.4; 129.3; 129.0; 128.5; 128.1; 128.0; 126.8; 112.4; 58.5; 28.3; 15.3. Mass spec (MH$^+$ 367). Analysis for C$_{25}$H$_{22}$N$_2$O; calculated, C 81.94, H 6.05, N 7.64; found C 81.74, H 6.26, N 7.46.

EXAMPLE 11

6-((4-Isopropoxy)phenyl,phenyl)methyl-2-phenyl-pyrimidine-4-ol, 11

Compound 11 was prepared in a manner similar to that employed in Example 6 using 4-isopropylbenzaldehyde in procedure 5. Purification was accomplished using column chromatography to provide the title compound as a solid (mp 102–108° C.). $^1$H-NMR (CDCl$_3$) δ 8.1 (m, 2H); 7.5 (m, 3H); 7.3 (m, 7H); 6.8 (m, 2H); 6.2 (s, 1H); (s, 1H); 4.5 (m, 1H); 1.3 (d, 6H). $^{13}$C-NMR (CDCl$_3$) δ 171.1; 165.9; 156.9; 156.6; 141.6; 133.0; 132.1; 132.0; 130.4; 129.4; 128.9; 128.5; 127.9; 126.8; 115.7; 112.3; 69.7; 58.0; 21.9. Mass spec (MH$^+$ 397). Analysis for C$_{26}$H$_{24}$N$_2$O$_2$; calculated, C 78.76, H 6.10, N 7.07; found C 79.89, H 6.11, N 6.81.

EXAMPLE 12

6-((4-Methoxy)phenyl,phenyl)methyl-2-phenyl-pyrimidine-4-ol, 12

Compound 12 was prepared in a manner similar to that employed in Example 6 using 4-methoxybenzaldehyde in procedure 5. Purification was accomplished using column chromatography to provide the title compound as a solid (mp 204–205° C.). $^1$H-NMR (CDCl$_3$) δ 8.2 (m, 2H); 7.5 (m, 3H); 7.3–7.2 (m, 7H); 6.9 (m, 2H); 6.2 (s, 1H); 5.4 (s, 1H); 3.8 (s, 3H). $^{13}$C-NMR (CDCl$_3$) δ 171.1; 165.9; 158.5; 156.6; 141.5; 133.3; 132.1; 132.0; 130.5; 129.3; 128.9; 128.5; 127.9; 126.8; 113.4; 112.3; 58.0; 55.2. Mass spec (MH$^+$ 369). Analysis for C$_{22}$H$_{20}$N$_2$O$_2$; calculated, C 78.24, H 5.47, N 7.60; found 78.02, H 5.57, N 7.52.

EXAMPLE 13

6-((4-Ethyl)phenyl,phenyl)methyl-2-phenyl-pyrimidine, 13

The title compound was prepared from compound 10 using Method F. Purification was accomplished using preparative TLC to provide compound 13 as an oil. $^1$H-NMR (CDCl$_3$) δ 8.69 (d, J=5.2 Hz, 1H), 8.42 (m, 2H), 7.45 (m, 3H), 7.34–7.24 (m, 5H), 7.16 (d, 4H), 7.01 (d, J=5.2 Hz, 1H), 5.61 (s, 1H), 2.63 (q, J=7.4 Hz, 2H), 1.22 (t, J=7.4 Hz, 3H). $^{13}$C-NMR (CDCl$_3$) δ 171.7; 164.5; 157.5; 142.9; 138.9; 137.8; 130.7; 129.4; 129.3; 128.5; 128.4; 128.1; 126.9; 119.0; 58.8; 28.3; 15.3. Mass spec (MH$^+$ 351).

EXAMPLE 14

6-((4-Ethoxy)phenyl,phenyl)methyl-2-phenyl-pyrimidine-4-ol, 14

The title compound was prepared using the procedures described in Example 6 using 4-ethoxybenzaldehyde in procedure 5. Purification was accomplished using column chromatography to provide the title compound as a solid (mp 193–196° C.). $^1$H-NMR (CDCl$_3$) δ 8.1 (m, 1H); 7.5 (m, 3H); 7.3–7.1 (m, 7H); 6.8 (m, 2H); 6.2 (s, 1H); 5.4 (s, 1H); 4.0 (m, 2H); 1.4 (t, 3H) $^{13}$C-NMR (CDCl$_3$) δ 171.1; 165.9; 157.9; 156.6; 141.5; 133.1; 132.1; 132.0; 130.4; 129.3; 128.9; 128.5; 127.9; 126.8; 114.4; 112.3; 63.3; 57.9 14.7. Mass spec (MH$^+$ 383). Analysis for C$_{25}$H$_{22}$N$_2$O$_2$; calculated, C 78.51, H 5.80, N 7.32; found C 77.72, H 6.00, N 6.95.

EXAMPLE 15

6-((4-n-Propyl)phenyl,phenyl)methyl-2-phenyl-pyrimidine-4-ol, 15

The title compound was prepared using the procedures described in Example 6 using 4-n-propylbenzaldehyde in procedure 5. Purification was accomplished using column chromatography to provide the title compound as a solid (mp 149–154° C.). $^1$H-NMR (CDCl$_3$) δ 8.1 (m, 2H); 7.5 (m, 3H); 7.3–7.1 (m, 9H); 6.2 (s, 1H); 5.4 (s, 1H); 2.6 (t, 2H); 1.6 (m, 2H); 0.9 (t. 3H). $^{13}$C-NMR (CDCl$_3$) δ 171.0; 165.8; 156.6; 141.43; 141.37; 138.4; 132.1; 132.0; 129.4; 129.3; 129.0; 128.6; 128.5; 127.9; 126.8; 112.4; 58.5; 37.6; 24.4; 13.8. Mass spec (MH$^+$ 381). Analysis for C$_{26}$H$_{24}$N$_2$O; calculated, C 82.07, H 6.36, N 7.36; found C 80.32, H 6.16, N 7.10.

EXAMPLE 16

6-(bis-(4-Methoxy)phenyl)methyl-2-phenyl-pyrimidine-4-ol, 16

The title compound was prepared using the procedures described in Example 8 using 4,4'-dimethoxyphenyl acetic acid. Purification was accomplished using column chromatography to provide the title compound as a solid (mp 190° C., dec). $^1$H-NMR (CDCl$_3$) δ 8.1 (m, 2H) 7.5 (m, 3H); 7.2 (m, 3H); 6.9 (m, 4H); 6.2 (s, 1H); 5.3 (s, 1H); 3.8 (s, 6H). $^{13}$C-NMR (CDCl$_3$) δ 171.3; 166.6; 158.5; 157.3; 133.8; 132.8; 131.7; 130.4; 128.9; 127.9; 113.9; 1 11.9; 57.1; 55.2. Mass spec (MH$^+$ 399). Analysis for C$_{25}$H$_{22}$N$_2$O$_3$; calculated, C 75.36, H 5.57, N 7.03; found C 74.02, H 6.06, N 7.08.

EXAMPLE 17

6-(1-(4-Isobutyl)phenyl-2-(2,4-difluoro)phenyl) ethyl-2-phenyl-pyrimidine-4-ol, 17

The title compound was prepared as in Example 3 using 2,4-difluorobenzyl bromide in Method C. Purification was accomplished using preparative TLC (2×) to provide compound 17. $^1$H-NMR (CDCl$_3$) δ 8.26 (m, 2H), 7.54 (m, 3H), 7.31 (d, J=8.0 Hz, 2H), 7.06 (d, J=8.0 Hz, 2H), 6.92 (dd, J=1.98.5 Hz, 1H), 6.71 (m, 1H), 6.61 (m, 1H), 6.25 (s, 1H), 4.09 (m, 1H), 3.63 (dd. J=8.5, 13.5 Hz, 1H), 3.27 (dd, J=6.6, 13.7 Hz, 1H), 2.41 (d, J=7.1 Hz, 2H), 1.82 (m, 1H), 0.86 (d, J=7.6 Hz, 6H). $^{13}$C-NMR (CDCl$_3$) δ 170.0; 165.7; 156.4; 140.6; 138.5; 132.2; 132.0; 132.0; 131.9; 131.8; 129.3; 128.6; 127.9; 111.0; 52.9; 44.9; 33.1; 30.6; 22.2. Mass spec (MH$^+$ 445).

EXAMPLE 18

6-((4-n-Propyl)phenyl,phenyl)methyl-2-phenyl-pyrimidine-4-ol (enantiomer 1, 18)

Enantiomers of compound 15 were separated using procedure 11 to obtain compound 18. Further purification was accomplished using column chromatography to provide the title compound as a solid (mp 149–154° C.). $^1$H-NMR (CDCl$_3$) δ 8.1 (m, 2H); 7.5 (m, 3H); 7.3–7.1 (m, 9H); 6.2 (s, 1H); 5.4 (s, 1H); 2.6 (t, 2H); 1.6 (m, 2H); 0.9 (t, 3H). $^{13}$C-NMR (CDCl$_3$) δ 171.0; 165.8; 156.6; 141.43; 141.37; 138.4; 132.1; 132.0; 129.4; 129.3; 129.0; 128.6; 128.5; 127.9; 126.8; 112.4; 58.5; 37.6; 24.4; 13.8. Mass spec (MH$^+$ 381). Analysis for C$_{26}$H$_{24}$N$_2$O; calculated, C 82.07, H 6.36, N 7.36; found C 80.32, H 6.16, N 7.10.

EXAMPLE 19

6-((4-Propyl)phenyl,phenyl)methyl-2-phenyl-pyrimidine-4-ol (enantiomer 2, 19)

Enantiomers of compound 15 were separated using procedure 11 to obtain compound 19. Further purification was accomplished using column chromatography to provide the title compound as a solid (mp 149–154° C.). $^1$H-NMR (CDCl$_3$) δ 8.1 (m, 2H); 7.5 (m, 3H); 7.3–7.1 (m, 9H); 6.2 (s, 1H); 5.4 (s, 1H); 2.6 (t, 2H); 1.6 (m, 2H); 0.9 (t, 3H). $^{13}$C-NMR (CDCl$_3$) δ 171.0; 165.8; 156.6; 141.43; 141.37; 138.4; 132.1; 132.0; 129.4; 129.3; 129.0; 128.6; 128.5; 127.9; 126.8; 112.4; 58.5; 37.6; 24.4; 13.8. Mass spec (MH$^+$ 381). Analysis for C$_{26}$H$_{24}$N$_2$O; calculated, C 82.07, H6.36, N7.36; found C 80.32, H 6.16, N 7.10.

EXAMPLE 20

6-(1-(4-Isobutyl)phenyl-1-(2-bromo)phenyl)methyl-2-phenyl-pyrimidine-4-ol

Compound 20 was prepared via the methods described in Example 5 using 2-bromobenzoic acid in procedure 8. Purification was accomplished using flash chromatography to provide the title compound. $^1$H-NMR (CDCl$_3$) δ 8.13 (m, 2H), 7.59 (m, 1H), 7.47 (m, 3H), 7.25 (m, 1H), 7.12 (m, 2H), 7.11 (s, 4H), 6.14 (s, 1H), 5.83 (s, 1H), 2.45 (d, J=7.1 Hz, 2H), 1.85 (m, 1H), 0.90 (d, J=6.6 Hz, 6H). $^{13}$C-NMR (CDCl$_3$) δ 169.9; 165.8; 156.5; 140.8; 140.5; 137.1; 133.2; 132.1; 132.0; 131.3; 129.4; 129.3; 128.9; 128.5; 128.0; 127.4; 125.7; 112.7; 57.5; 45.0; 30.0; 22.3. (MH$^+$ 473.5).

EXAMPLE 21

6-((4-Isopropoxy)phenyl,phenyl)methyl-2-phenyl-pyrimidine-4-ol (enantiomer 1, 21)

Compound 11 was separated into enantiomers using procedure 11 to obtain compound 21. $^1$H-NMR (CDCl$_3$) δ 8.1 (m, 2H); 7.5 (m, 3H); 7.3 (m, 7H); 6.8 (m, 2H); 6.2 (s, 1H); 5.4 (s, 1H); 4.5 (m, 1H); 1.3 (d, 6H). $^{13}$C-NMR (CDCl$_3$) δ 17.1; 165.9 156.9; 156.6; 141.6; 133.0; 132.1; 132.0; 130.4; 129.4; 128.9; 128.5; 127.9; 126.8; 115.7; 112.3; 69.7; 58.0; 21.9.

EXAMPLE 22

6-((4-Isopropoxy)phenyl,phenyl)methyl-2-phenyl-pyrimidine-4-ol (enantiomer 2, 22)

Compound 11 was separated into enantiomers using procedure 11 to obtain compound 22. $^1$H-NMR (CDCl$_3$) δ 8.1 (m, 2H); 7.5 (m, 3H); 7.3 (m, 7H); 6.8 (m, 2H); 6.2 (s, 1H); 5.4 (s, 1H); 4.5 (m, 1H); 1.3 (d, 6H). $^{13}$C-NMR (CDCl$_3$) δ 171.1; 165.9; 156.9; 156.6; 141.6; 133.0; 132.1; 132.0; 130.4; 129.4; 128.9 128.5; 127.9; 126.8; 115.7; 112.3; 69.7; 58.0; 21.9.

EXAMPLE 23

6-((4-Isopropyl)phenyl,phenyl)methyl-2-phenyl-1-methyl-pyrimidine-4-ol, 23

The β-keto ester used in Example 6 was alkylated with methyl iodide using procedure 10. The pyrimidine was formed by Method A. Further purification was accomplished using column chromatography to provide the title compound as a solid (mp>200° C.). $^1$H-NMR (CDCl$_3$) δ 8.15 (d, 2H); 7.3 (m, 2H); 5.6 (s, 1H); 2.9 (m, 1H); 2.25 (s, 3H); 1.23 (d, 6H). $^{13}$C-NMR (CDCl$_3$) δ 4.596; 6.126; 19.435; 29.122; 49.351; 115.345; 121.905; 122.195; 122.743; 123.786; 124.468; 124.946; 125.110; 127.140; 127.822; 134.375; 137.471; 142.816; 147.746; 159.800; 160.733. Mass spec (MH$^+$ 395). Analysis for C$_{27}$H$_{26}$N$_2$O+0.8 H$_2$O; calculated, C 79.30, H 6.80, N 6.85; found C 79.22, H 6.67, N 6.43.

EXAMPLE 24

6-((4-Butyl)phenyl,phenyl)methyl-2-phenyl-pyrimidine-4-ol, 24

Compound 24 was prepared via the methods of Example 6 using 4-n-butyl benzaldehyde. Purification was accomplished using column chromatography to provide the title compound as a solid (mp 118–120° C.). $^1$H-NMR (CDCl$_3$) δ 8.2 (m, 2H); 7.5 (m, 3H); 7.3 (m, 5H); 7.1 (m, 4H); 6.2 (s, 1H); 5.4 (s, 1H); 2.6 (t, 2H); 1.6 (m, 2H); 1.4 (m, 2R); 0.9 (t,3H). $^{13}$C-NMR (CDCl$_3$) δ 171.0; 165.9; 156.6; 141.6; 141.4; 138.3; 132.1; 131.9; 129.4; 129.3; 128.9; 128.6; 128.5; 128.0; 126.8; 112.4; 58.5; 35.1; 33.5; 22.3; 13.8. Mass spec (MH$^+$ 395). Analysis for C$_{27}$H$_{26}$N$_2$O; calculated, C82.20, H6.64, N7.10; found C 81.99, H 6.80, N 6.96.

EXAMPLE 25

6-(bis-(4-Ethoxy)phenyl)methyl-2-phenyl-pyrimidine-4-ol, 25

Compound 25 was prepared as in Example 8 using 4,4'-diethoxybenzoic acid in procedure 4. Purification was accomplished using column chromatography to provide the title compound as a solid (mp 167–173° C.). $^1$H-NMR (CDCl$_3$) δ 13.0 (s, 1H); 8.1 (m, 2H); 7.5 (m, 3H); 7.2 (m, 4H); 6.8 (m, 4H); 6.2 (s, 1H); 5.3 (s, 1H); 40. (m, 4H); 1.4(t, 6H). $^{13}$C-NMR (CDCl$_3$) δ 171.5; 165.8; 157.9; 156.5; 133.5; 132.1; 132.0; 130.3; 129.0; 127.9; 114.4; 112.2, 63.3; 57.2; 14.7. Mass spec (MH$^+$ 395). Analysis for C$_{27}$H$_{26}$N$_2$O$_3$; calculated, C 76.03, H 6.14, N 6.57; found C 75.79, H 6.24, N 6.48.

EXAMPLE 26

The compounds of the present invention were assayed for cPLA$_2$ activity using cPLA$_2$ enzyme from the cytosolic extraction of U937 cells (all procedures carried out on ice).

i. Cytosolic Extraction of U937 Cells

U937 cells were harvested and spun for five minutes at 1000 g and washed at least three times in extraction buffer (140 mM NaCl, 5 mM KCl, 2 mM EDTA, 25 mM Tris, pH 7.4 solution). The cells were then suspended in buffer (1×10$^8$ cells/mL) and protease inhibitors were added to achieve the following concentrations: 100 μM leupeptin, 50 μM pepstatin, and 1 mM PMSF. The cells were placed in a N$_2$ cavitation bomb and put under pressure to 600 psi for 20 minutes in a cold room. The suspension was released and collected, then spun at 100,000 g for 60 minutes at 4° C. The supernatent was collected, filtered through a 0.22 μM filter, diluted to 50% with glycerol, aliquoted and stored at −20° C.

ii. cPLA$_2$ Enzyme Assay Using U937 Cytosolic Extract as Enzyme Source a. Materials and Chemicals:

Phosphatidylcholine L-α-1-palmitoyl-2-arachidonyl-1 [$^{14}$C] was obtained from New England Nuclear (NEC-765). 1,2-dioleyl-glycerol was obtained from Avanti Polar Lipids (800811 in CHCl$_3$). The substrate buffer was 150 mM NaC: and 50 mM HEPS a t pH 7.5. 100 mg/mL BSA (ICN 823234) was made up in water. The assay buffer was 150 mM NaCl, 50 mM BEPES at pH 7.5, 1 mM CaCl$_2$ and 1 mM 2-ME. Dole's Reagent: 2-propanol/heptane/0.5 M H$_2$SO$_4$ (40:10:1) containing 10 μg/mL stearic acid. Silica gel was 100–200 μm (70–150 mesh) (obtained from Universal Scientific Inc. 02760). Ready Safe® scintillation cocktail, 96-well deep well plates (No. 267007) and foil seals for microtiler plates (o. 538619) were all obtained from Beckman Scientific. Nunc microtiter plates were also used along with 7 mL size scintillation vials and tops.

b. Instruments:

Hamilton Microlab AT Plus was used with a 37° C. incubator and a Beckman scintillation counter.

C. Hamilton At Plus Programs:

The Hamilton Microlab AT Plus was used to dilute compounds in DMSO from a 80× highest dose 1:5 dilutions for a total of5 concentrations (80× of each dose).

The Hamilton Microlab AT Plus runs the PLA$_2$ assay by pipetting the DMSO dilutions into diluted extract in assay buffer (1–3 μL/well—determined by lot of extraction) into a plate for a preincubation of 20 min at 37° C. This mixture is then pipetted into the radiolabeled liposomes (substrate) starting the reaction. The program also stops the reactions, does the heptane extractions, and transfers it to the silica gel.

d. Procedure:

Preparation of Substrate:

23 μL of the radiolabeled substrate was pipetted into a glass test tube and 3.1 μL of 1,2-dioleylglycerol (using a Hamilton syringe pipette) was added. Next, the solution was gently dried under an inert gas stream. The volume of the solution was increased to 1 mL using substrate buffer. The solution was then sonicated with a Branson sonifier for 2 min. at 50% max setting and 40 μL of a 100 mg/mL BSA solution was added. The solution was kept cold, on ice at 4° C.

Preparation of compounds:

To a 96-well Nunc Polysorp plate was pipetted 80 μL of DMSO into wells B1, B7, C1, C7, D1, D7. Into each of these wells was added 20 μL of a 10 mM stock solution of 6 test compounds in DMSO. The Hamilton Microlab diluted each of the test compound in DMSO (⅕) in serial dilutions, which yielded a total of five concentrations. Next, the program diluted the DMSO serial dilutions into an assay buffer containing U937 extract (5 μL compound+295 μL diluted enzyme). Then the plate was placed in 37° C. for 20 min of preincubation. In the same plate, controls with assay buffer alone were added and also U937 extract diluted in the assay buffer containing 50 mM EGTA with no calcium added. During preincubation of enzyme. with the test compounds, a deepwell plate was prewarmed and at 37° C. The substrate (10 μL/well) was pipetted in to this deepwell plate before the preincubation time was up.

Reaction Begins:

After the preincubation time was complete, the Hamilton mixed and added 30 μL of each test compound/extract to wells containing the substrate. After the reaction started, the plate was placed back to be kept at 37° C. The plate containing the reaction mixtures was incubated at 37° C. for 15 min.

Afterwards, the Hamilton added Dole's reagent to quench the reactions (400 μL). Heptane was then added (240 μL) followed by H$_2$O (200 μL). Next, the corresponding deepwell plate for each reaction tube was prepared by adding a slurry of 60 mg silica gel and 200 μL heptane. The Hamilton then pipetted 280 μL of the top layer (heptane phase) from the reaction plate to a silica gel plate. The silica gel plate was then sealed with foil seal tops. The plate was mixed vigorously on a microtiter plate shaker and then centrifuged at 1000 g for 1 min. The Hamilton transferred 400 μL from each well to 7 mL scintillation vials. The vials were then counted after the addition of 4 mL Ready Safe Beckman scintillation cocktail. Using this method, the inhibition of cPLA$_2$ by the compounds of the instant invention were assessed.

All publications, patents and patent applications mentioned in this specification are herein incorporated by reference into the specification to the same extent as if each individual publication, patent or patent application was specifically and individually indicated to be incorporated herein by reference for all purposes.

Although the foregoing invention has been described in some detail by way of illustration and example for purposes of clarity of understanding, it will be obvious that certain changes and modifications may be practiced within the scope of the appended claims.

What is claimed is:

1. A compound having the formula:

(I)

wherein,

R$^1$ is a member selected from the group consisting of C$_1$–C$_6$ alkyl, substituted C$_1$–C$_6$ alkyl, C$_1$–C$_6$ alkoxy, substituted C$_1$–C$_6$ alkoxy, C$_1$–C$_6$ cycloalkyl, substituted C$_3$—C$_6$ cycloalkyl, and halogen;

R$^2$ is a member selected from the group consisting of phenyl, substituted phenyl, benzyl, substituted benzyl, C$_3$–C$_7$ cycloalkyl, and substituted C$_3$–C$_7$ cycloalkyl;

R$^3$ is a member selected from the group consisting of hydrogen and C$_1$–C$_6$ alkyl;

R$^4$ is a member selected from the group consisting of —H, —OH, —N$_3$ and —NHCOCH$_3$; and pharmaceutically acceptable salts thereof.

2. A compound in accordance with claim 1, wherein R$^1$ is C$_1$–C$_6$ alkyl.

3. A compound in accordance with claim 1, wherein R$^1$ is C$_1$–C$_6$ alkoxy.

4. A compound in accordance with claim 1, wherein R$^2$ is phenyl or substituted phenyl.

5. A compound in accordance with claim 1, wherein R$^2$ is benzyl or substituted benzyl.

6. A compound in accordance with claim 1, wherein R$^1$ is C$_1$–C$_6$ alkyl, R$^3$ is H, and R$^4$ is OH.

7. A compound in accordance with claim 1, wherein R$^1$ is C$_1$–C$_6$ alkoxy, R$^3$ is H, and R$^4$ is OH.

8. A compound in accordance with claim 1, wherein R$^2$ is phenyl or substituted phenyl, R$^3$ is H, and R$^4$ is OH.

9. A compound in accordance with claim 1, wherein R$^2$ is benzyl or substituted benzyl, R$^3$ is H, and R$^4$ is OH.

10. A pharmaceutical composition comprising a compound of formula (I)

(I)

wherein,

R$^1$ is a member selected from the group consisting of C$_1$–C$_6$ alkyl, substituted C$_1$–C$_6$ alkyl, C$_1$–C$_6$ alkoxy, substituted C$_1$–C$_6$ alkoxy, C$_3$–C$_6$ cycloalky substituted C$_3$–C$_6$ cycloalkyl, and halogen;

R$^2$ is a member selected from the group consisting of phenyl, substituted phenyl, benzyl, substituted benzyl, C$_3$–C$_7$ cycloalkyl, and substituted C$_3$–C$_7$ cycloalkyl;

R³ is a member selected from the group consisting of hydrogen and $C_1$–$C_6$ alkyl;

R⁴ is a member selected from the group consisting of —H, —OH, —N₃ and —NHCOCH₃;

or a pharmaceutically acceptable salt thereof in unit dosage form with a pharmaceutically acceptable carrier.

11. A composition in accordance with claim 10, wherein R¹ is $C_1$–$C_6$ alkyl.

12. A composition in accordance with claim 10, wherein R¹ is $C_1$–$C_6$ alkoxy.

13. A composition in accordance with claim 10, wherein R² is phenyl or substituted phenyl.

14. A composition in accordance with claim 10, wherein R² is benzyl or substituted benzyl.

15. A composition in accordance with claim 10, wherein R¹ is $C_1$–$C_6$ alkyl, R³ is H, and R⁴ is OH.

16. A composition in accordance with claim 10, wherein R¹ is $C_1$–$C_6$ alkoxy, R³ is H, and R⁴ is OH.

17. A composition in accordance with claim 10, wherein R² is phenyl or substituted phenyl, R³ is H, and R⁴ is OH.

18. A composition in accordance with claim 10, wherein R² is benzyl or substituted benzyl, R³ is H, and R⁴ is OH.

* * * * *